United States Patent [19]
Colpaert et al.

[11] Patent Number: 5,661,172
[45] Date of Patent: Aug. 26, 1997

[54] USE OF EFAROXAN AND DERIVATIVES THEREOF FOR THE TREATMENT OF ALZHEIMER'S DISEASE

[75] Inventors: Francis Colpaert, Castres; Michael Briley, Gaillac; Thierry Imbert, Viviers-les-Montagnes, all of France

[73] Assignee: Pierre Fabre Medicament, Boulonge, France

[21] Appl. No.: 581,516

[22] PCT Filed: Jul. 7, 1994

[86] PCT No.: PCT/FR94/00841

§ 371 Date: Jan. 11, 1996

§ 102(e) Date: Jan. 11, 1996

[87] PCT Pub. No.: WO95/01791

PCT Pub. Date: Jan. 19, 1995

[30] Foreign Application Priority Data

Jul. 9, 1993 [FR] France ................................ 93/08497

[51] Int. Cl.$^6$ .................................................. A61K 31/415
[52] U.S. Cl. ................................................................ 514/402
[58] Field of Search ................................................. 514/402

[56] References Cited

U.S. PATENT DOCUMENTS 4,855,385 8/1989 Kester et al. ............................ 514/332

*Primary Examiner*—Theodore J. Criares
*Attorney, Agent, or Firm*—The Firm of Gordon W. Hueschen

[57] ABSTRACT

The present invention relates to the use of efaroxan and derivatives for the treatment of Alzheimer's disease.

5 Claims, No Drawings

USE OF EFAROXAN AND DERIVATIVES THEREOF FOR THE TREATMENT OF ALZHEIMER'S DISEASE

This application is filed under 35 U.S.C. 371 of PCT/FR94/00841, filed 07 Jul. 1994, which claims priority of application 93/08497 filed in France 09 Jul. 1993.

The present invention relates to the use of efaroxan and derivatives for the treatment of Alzheimer-like senile dementia, pre-Alzheimer's syndrome, progressive supranuclear palsy and other neurodegenerative diseases.

Alzheimer's disease is a progressive neurodegenerative disease particularly, but not exclusively, affecting the central cholinergic system (Meynert's nucleus basalis) manifested by a loss of cognitive faculties, a loss of intellectual capacities, and behavioral and personality disorders.

There is currently no satisfactory treatment either for treating the symptoms or for slowing its advancement. Diagnosis of the disease is difficult, and one can never be certain about diagnosing Alzheimer's disease per se. It is in particular the anatomohistological analysis performed post-mortem by, inter alia, the revelation of extraneuronal senile plaques and intraneuronal neurofibrillar networks which makes it possible to diagnose Alzheimer's disease unambiguously. A loss of cellular bodies and a depletion of neurotransmitters, in particular acetylcholine, are also associated therewith. In the absence of this histological and biochemical proof, the clinical characteristics lead to the diagnosis of a pre-Alzheimer-like neurodegenerative disease.

"Progressive Supranuclear Palsy" (PSP) is a non-hereditary evolutive neurodegenerative disease which appears late and involves perturbations of several neurotransmitters. PSP is characterized by dementia with postural instability, rigidity, associated bradykinesia, accompanied by supranuclear ophthalmoplegia. This disease appears in about 4% of patients suffering from Parkinsonism. There is currently no treatment for this disease. Palliative or symptomatological therapies do not have a satisfactory effect.

It is known that efaroxan, 2-(2-ethyl-2,3-dihydrobenzofuranyl)-2-imidazoline, possesses antagonist properties with respect to $\alpha_2$-adrenergic receptors. This compound is described in patent application GB-2,102,422 along with its therapeutic application as an anti-depressant and antimigraine medicinal product.

This compound and derivatives thereof are also described in patent application WO 92/05171 in which the action of the levorotatory enantiomer for treating diabetes and the action as a potassium channel blocking agent are demonstrated.

The present invention relates to the use of efaroxan and derivatives thereof for the preparation of a medicinal product intended for the treatment of Alzheimer-like senile dementia, pre-Alzheimer's syndrome, progressive supranuclear palsy and other neurodegenerative diseases.

The expression efaroxan and derivatives thereof is understood to mean the compound of formula I in which $R_1$ represents a hydrogen atom or a linear or branched $C_1$–$C_6$ alkyl radical, $R_2$ represents a hydrogen atom or a methyl, chloro, bromo or fluoro group, and $R_3$ represents a hydrogen atom or a methyl, hydroxyl, methoxy, fluoro, chloro or bromo group, and the therapeutically acceptable salts thereof, the racemic mixture thereof or the optically active isomers thereof.

Advantageously, $R_2$ and $R_3$ represent a hydrogen atom and $R_1$ represents an ethyl, n-propyl or i-propyl group.

The compound of general formula I is preferably chosen from the following compounds:

2-(2-ethyl-2,3-dihydrobenzofuranyl)-2-imidazoline, 2-(2-n-propyl-2,3-dihydrobenzofuranyl)-2-imidazoline, 2-(2-i-propyl-2,3-dihydrobenzofuranyl)-2-imidazoline.

PHARMACOLOGICAL STUDY

A study on the activity of efaroxan on rat memory functions was performed in accordance with the described conditions (P. CHOPIN and M. BRILEY, Psychopharmacology 106, 26 (1992)).

When administered before the first passive avoidance behavior training session, scopolamine, a central antagonist, induces a dose-dependent amnesia which may be measured 48 hours later during a second session.

The administration of efaroxan, 30 minutes before the second session, decreases the amnesia induced by scopolamine, thus showing an increase in mnemonic activity by stimulation of the memory functions.

The table below shows the effect of efaroxan in the presence of scopolamine, in a dose-dependent manner, in increasing the time required for the rat to pass from a lit compartment to a dark compartment where it receives a small electric shock. The percentage of the effect is given in the 3rd column.

|  | Dose mg/kg entrance i.p. | delay time (sec) | % significant effect |
| --- | --- | --- | --- |
| Efaroxan | 0 | 28.6 ± 11.6 |  |
|  | 0.04 | 38.3 ± 16.2 | +34 |
|  | 0.16 | 56.0 ± 15.3 | +96 |

The above results show the advantage of using efaroxan as a medicinal product in order to improve the memory functions and in order to improve the symptomatology of Alzheimer's disease.

PHARMACEUTICAL STUDY

The pharmaceutical compositions are administered orally in the form of gelatin capsules or tablets containing a dose of 1 to 100 mg of active principle, more particularly of 2, 5 and 20 mg per capsule, or intravenously in the form of an injectable solution containing a dose of 0.1 to 10 mg of efaroxan.

CLINICAL STUDY

Efaroxan was administered at a dose of 2 to 20 mg per dosage intake per day for 6 months, to patients who had manifested memory disorders, symptoms of cognitive deficiencies and behavioral disorders suggesting a pre-Alzheimer syndrome. The results on the overall symptomatology showed a benefit in 30% of the cases.

PSP CLINICAL STUDY 12 patients suffering from PSP received efaroxan, at a dose of 2 mg 3 or 4 times per day for 4 weeks, in comparison with an identical period during which a placebo was administered.

After the study, the comparison is in favor of the period treated with efaroxan, during which the symptomatology observed is improved, as are the usual grade scores and likewise the cognitive and mood tests for more than 30% of the cases.

We claim:

1. Method for the treatment of Alzheimer-like senile dementia, pre-Alzheimer's syndrome, and progressive supranuclear palsy, in a mammal suffering therefrom, comprising the step of administering to the said mammal an amount of a compound selected from those of formula I

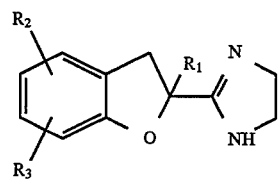

in which $R_1$ represents hydrogen or linear or branched $C_1$–$C_6$ alkyl, $R_2$ represents hydrogen or methyl, chloro, bromo, or fluoro, and $R_3$ represents hydrogen or methyl, hydroxyl, methoxy, fluoro, chloro, or bromo, and a therapeutically-acceptable salt thereof, a racemic mixture thereof, and an optically-active isomer thereof, which is effective for said purpose.

2. Method of claim 1, wherein $R_2$ and $R_3$ represent a hydrogen atom.

3. Method of claim 1, wherein $R_1$ represents an ethyl, n-propyl, or i-propyl group.

4. Method of claim 2, wherein $R_1$ represents an ethyl, n-propyl, or i-propyl group.

5. Method of claim 1, wherein the compound is selected from the group consisting of:

2-(2-ethyl-2,3-dihydrobenzofuranyl)-2-imidazoline, 2-(2-n-propyl-2,3-dihydrobenzofuranyl)-2-imidazoline, and 2-(2-i-propyl-2,3-dihydrobenzofuranyl)-2-imidazoline.

* * * * *

UNITED STATES PATENT AND TRADEMARK OFFICE
CERTIFICATE OF CORRECTION

PATENT NO. : 5,661,172
DATED : August 26, 1997
INVENTOR(S) : F. Colpaert, M. Briley, T. Imbert It is certified that error appears in the above-identified patent and that said Letters Patent is hereby corrected as shown below:

Column 2, line 40: "nmemonic" should read -- mnemonic --.

Signed and Sealed this

Twentieth Day of January, 1998

Attest:

BRUCE LEHMAN

Attesting Officer

Commissioner of Patents and Trademarks